United States Patent
Touge et al.

(10) Patent No.: US 7,880,025 B2
(45) Date of Patent: Feb. 1, 2011

(54) RUTHENIUM SILYL-ARENE COMPLEX, AND METHOD FOR PRODUCTION THEREOF

(75) Inventors: Taichiro Touge, Kanagawa (JP); Hideki Nara, Kanagawa (JP); Takahiro Fujiwara, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 0 days.

(21) Appl. No.: 12/782,153

(22) Filed: May 18, 2010

(65) Prior Publication Data

US 2010/0298588 A1   Nov. 25, 2010

(30) Foreign Application Priority Data

May 19, 2009   (JP) .............................. 2009-121013

(51) Int. Cl.
*C07F 15/00* (2006.01)
*B01J 31/00* (2006.01)

(52) U.S. Cl. .......................... 556/12; 502/152; 502/158
(58) Field of Classification Search .................. 556/12; 502/152, 158
See application file for complete search history.

(56) References Cited

U.S. PATENT DOCUMENTS 6,544,923 B1 * 4/2003 Huang et al. ................. 502/159

FOREIGN PATENT DOCUMENTS

WO    01/14060 A2    3/2001

OTHER PUBLICATIONS

P. Xie et al., "The Crystal Structure of BRAF in Complex with an Organoruthenium Inhibitor Reveals a Mechanism for Inhibition of an Active Form of BRAF Kinase", Biochemistry, 48(23), pp. 5187-5898 (2009).
M. Ito et al., "Synthesis and Structure of Novel (h1:h6-Aminoalkylarene)Ru11 Complexes" Chemistry Letters, 38(1), pp. 98-99 (2009).

* cited by examiner

*Primary Examiner*—Porfirio Nazario Gonzalez
(74) *Attorney, Agent, or Firm*—Peter F. Corless; Christine C. O'Day; Edwards Angell Palmer & Dodge LLP

(57) ABSTRACT

The present invention is to provide a ruthenium complex having a novel arene moiety, which has improved solubility in various solvents, and a method for production thereof.

The present invention relates to a novel ruthenium complex having an arene moiety, which has a trisubstituted silyl group introduced to the arene moiety, and a method for production thereof.

5 Claims, No Drawings

RUTHENIUM SILYL-ARENE COMPLEX, AND METHOD FOR PRODUCTION THEREOF

CROSS-REFERENCES TO RELATED APPLICATIONS

This application claims under 35 U.S.C. §119(a) the benefit of Japanese Application No. 2009-121013 filed May 19, 2009 the entire contents of which is incorporated herein by reference.

TECHNICAL FIELD

The present invention relates to a ruthenium silyl-arene complex which is important as a precursor for the synthesis of catalysts, medicines or functional materials, and a method for production thereof.

BACKGROUND ART

Ruthenium-arene (6-membered) complexes have been used as precursors of hydrogenation catalysts or hydrogen transfer catalysts. Recently, these ruthenium-arene complexes are also used as precursors of anti-tumor agents, thin film electrode materials for semiconductor devices or the like, and thus the demand for the complexes is ever increasing.

These ruthenium-arene complexes are generally produced by refluxing corresponding 1,3- or 1,4-cyclohexadienes and ruthenium (III) trichloride tetrahydrate in ethanol or methanol (see J. Chem. Soc., Dalton Trans (1974) p. 233).

Another method, under high temperature [RuCl$_2$(p-cymene)]$_2$ was melted together with hexamethylbenzene, durene (1,2,4,5-tetramethylbenzene) or the like, which have higher boiling points than that of p-cymene, and allowing the compounds to react and exchange the arene moieties (see Inorg. Chem., 19 (1980) p. 1014-1021; and Inorg. Synth., 21 (1982) p. 74-78).

DISCLOSURE OF THE INVENTION

Problems to be Solved by the Invention

However, the known dimer complexes obtained by the above methods, such as [RuCl$_2$(benzene)]$_2$, [RuCl$_2$(p-cymene)]$_2$, [RuCl$_2$(mesitylene)]$_2$ and the like which have alkylbenzenes for the arene moiety, generally have poor solubility in various solvents. Therefore, upon using these dimer complexes as the precursors of hydrogenation catalysts or hydrogen transfer catalysts, there have been limitation based on their poor solubility. Accordingly, when the solvent is used for the preparation of the catalysts, a large amount of solvent is required, in view of the reactor efficiency in an industrial scale or the environmental burden.

It is an object of the present invention to provide a ruthenium complex having a novel arene moiety, which has improved solubility in various solvents, and a method for production thereof.

Means for Solving the Problems

Thus, the inventors of the present invention made a thorough investigation to solve the problems mentioned above. They found that when a trisubstituted silyl group is introduced to the arene moiety of a ruthenium-arene complex, a ruthenium-arene complex having enhanced solubility in various solvents can be obtained.

The present invention includes the following items:

[1] A ruthenium complex represented by the following formula (1):

$$[RuX_2(L^1)]_2 \qquad (1)$$

wherein X represents a halogen atom; L$^1$ represents an aromatic compound represented by the following formula (2):

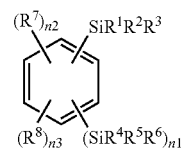

(2)

(wherein R$^1$, R$^2$, R$^3$, R$^4$, R$^5$ and R$^6$ each independently represent an alkyl group having 1 to 10 carbon atoms, a cycloalkyl group having 3 to 6 carbon atoms, or a phenyl group which may be substituted with an alkyl group having 1 to 10 carbon atoms or an alkoxy group having 1 to 10 carbon atoms; R$^7$ and R$^8$ each independently represent a hydrogen atom, an alkyl group having 1 to 10 carbon atoms, or an alkoxy group having 1 to 10 carbon atoms; and n1, n2 and n3 each represent 0 or 1).

[2] A method for producing the ruthenium complex as described in the above [1], the method including reacting ruthenium halide or a hydrate thereof with a diene compound represented by the following formula (3) in a solvent:

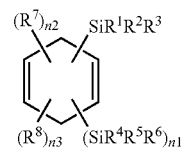

(3)

wherein R$^1$, R$^2$, R$^3$, R$^4$, R$^5$ and R$^6$ each independently represent an alkyl group having 1 to 10 carbon atoms, a cycloalkyl group having 3 to 6 carbon atoms, or a phenyl group which may be substituted with an alkyl group having 1 to 10 carbon atoms or an alkoxy group having 1 to 10 carbon atoms; and R$^7$ and R$^8$ each independently represent a hydrogen atom, an alkyl group having 1 to 10 carbon atoms, or an alkoxy group having 1 to 10 carbon atoms; and n1, n2 and n3 each represent 0 or 1.

[3] The method for producing the ruthenium complex as described in the above [2], including allowing the compounds to react in the presence of a base.

[4] The method for producing the ruthenium complex as described in the above [2] or [3], wherein the ruthenium halide is ruthenium chloride.

Effects of the Invention

The ruthenium-arene complex obtained by the present invention may be widely used for hydrogenation catalysts or hydrogen transfer catalysts. When these dimer complexes are used as the precursors of catalysts, owing to their good solubility, more various kinds of solvents for catalyst preparation may be used, as compared with those known dimer complexes which have alkylbenzene for the arene moiety. Further, since the solubility is improved, there is no need to use a large amount of solvent, and thus it is highly advantageous in that not only the reactor efficiency in an industrial scale is improved, but also the environmental burden is reduced.

MODES FOR CARRYING OUT THE INVENTION

Hereinafter, the present invention will be specifically described.

In the aromatic compound represented by the formula (2) and the diene compound represented by the formula (3), the alkyl group having 1 to 10 carbon atoms represented by $R^1$, $R^2$, $R^3$, $R^4$, $R^5$ and $R^6$ may be a straight-chained or branched alkyl group, and specific examples include a methyl group, an ethyl group, an n-propyl group, an isopropyl group, an n-butyl group, an s-butyl group, an isobutyl group, a t-butyl group, an n-pentyl group, an n-hexyl group, an n-heptyl group, an n-octyl group, an n-nonyl group, an n-decyl group, and the like. A preferred alkyl group may be a straight-chained or branched alkyl group having 1 to 5 carbon atoms.

In the aromatic compound represented by the formula (2) and the diene compound represented by the formula (3), the cycloalkyl group having 3 to 6 carbon atoms represented by $R^1$, $R^2$, $R^3$, $R^4$, $R^5$ and $R^6$ may be a cyclopropyl group, a cyclobutyl group, a cyclopentyl group, or a cyclohexyl group.

In the aromatic compound represented by the formula (2) and the diene compound represented by the formula (3), examples of the alkoxy group having 1 to 10 carbon atoms represented by $R^1$, $R^2$, $R^3$, $R^4$, $R^5$ and $R^6$ include a methoxy group, an ethoxy group, an n-propoxy group, an isopropoxy group, an n-butoxy group, an s-butoxy group, an isobutoxy group, a t-butoxy group, an n-pentyloxy group, an n-hexyloxy group, an n-heptyloxy group, an n-octyloxy group, an n-nonyloxy group, an n-decyloxy group, and the like. A preferred alkoxy group may be a straight-chained or branched alkoxy group having 1 to 5 carbon atoms.

In the aromatic compound represented by the formula (2) and the diene compound represented by the formula (3), the phenyl group which may be substituted with an alkyl group having 1 to 10 carbon atoms or an alkoxy group having 1 to 10 carbon atoms, represented by $R^1$, $R^2$, $R^3$, $R^4$, $R^5$ and $R^6$, may be a phenyl group which may be substituted with an alkyl group having 1 to 10 carbon atoms or alkoxy group having 1 to 10 carbon atoms such as the alkyl group or alkoxy group mentioned above. A preferred phenyl group which may be substituted may be an unsubstituted phenyl group, or a phenyl group substituted with an alkyl group having 1 to 10, preferably 1 to 5, carbon atoms, and examples thereof include a phenyl group, a 4-methylphenyl group, a 4-isopropylphenyl group, and the like.

In the aromatic compound represented by the formula (2) and the diene compound represented by the formula (3), a preferred example of the group represented by $R^1$, $R^2$, $R^3$, $R^4$, $R^5$ and $R^6$ may be a straight-chained or branched alkyl group having 1 to 10, more preferably 1 to 5, carbon atoms.

In the aromatic compound represented by the formula (2) and the diene compound represented by the formula (3), the alkyl group having 1 to 10 carbon atoms or alkoxy group having 1 to 10 carbon atoms, represented by $R^7$ and $R^8$ may be an alkyl group or alkoxy group such as mentioned above. A preferred combination of $R^7$ and $R^8$ may be such that one or both of $R^7$ and $R^8$ is a hydrogen atom or an alkyl group having 1 to 10 carbon atoms. Preferred examples of the alkyl group having 1 to 10 carbon atoms for $R^7$ and $R^8$, include a methyl group, an ethyl group, an isopropyl group, and the like.

In the aromatic compound represented by the formula (2) and the diene compound represented by the formula (3), the trisubstituted silyl group represented by $SiR^1R^2R^3$ and $SiR^4R^5R^6$ is a silyl group in which the three valencies of a silicon atom are bound to carbon atoms, and the carbon atom which may be bound to the silicon atom may be any of a saturated or unsaturated aliphatic atom, a saturated or unsaturated alicyclic atom, and an aromatic atom. Specific examples of a preferred trisubstituted silyl group include, for example, a trialkyl-substituted silyl group such as a trimethylsilyl group, a triethylsilyl group, a triisopropylsilyl group or a tert-butyldimethylsilyl group; a triaryl-substituted silyl group such as a triphenylsilyl group; an aryl-alkyl-substituted silyl group such as a diphenylmethylsilyl group or a dimethylphenylsilyl group; and the like.

Furthermore, preferred examples of the aromatic compound represented by the formula (2) include trialkyl-substituted, trisubstituted silylbenzene having a trialkyl-substituted, trisubstituted silyl group, such as trimethylsilylbenzene, trimethylsilyltoluene, trimethylsilylxylene, triethylsilylbenzene, triethylsilyltoluene, triethylsilylxylene, t-butyldimethylsilylbenzene, t-butyldimethylsilyltoluene or t-butyldimethylsilylxylene; an alkyl-substituted benzene having a trisubstituted silyl group which is substituted with at least one (substituted) phenyl group, such as triphenylsilylbenzene, triphenylsilyltoluene, triphenylsilylxylene, dimethylphenylsilylbenzene, dimethylphenylsilyltoluene or dimethylphenylsilylxylene; and the like.

The benzene ring may have at least one trisubstituted silyl group, and the benzene ring may also have two or three or more trisubstituted silyl groups. The preferred number of the trisubstituted silyl groups is one or greater, and more preferably one or two. When the benzene ring is substituted with a plurality of trisubstituted silyl groups, each of the trisubstituted silyl groups may be same or different.

The halogen atom for X in the ruthenium complex represented by the formula (1) may be a chlorine atom, a bromine atom, an iodine atom, or the like. A preferred halogen atom may be a chlorine atom.

In regard to the method for producing the ruthenium-arene complex of the present invention, an intended ruthenium-arene complex may be produced according to a method described in, for example, J. Chem. Soc., Dalton Trans (1974) p. 233; Organic & Biomolecular Chemistry (2007), p. 1093; or the like, by reacting a 1,4-cyclohexadiene derivative represented by the formula (3) with ruthenium chloride trihydrate, in the presence of a base such as $NaHCO_3$ or in the absence of a base, in an alcohol solvent such as 2-methoxyethanol.

The solvent used herein is not particularly limited, but an aliphatic alcohol such as methanol, ethanol, isopropanol, n-butanol or cyclohexanol; an aralkyl alcohol such as benzyl alcohol; diols such as ethylene glycol, 1,2-propanediol, 2-methoxyethanol or ethylene glycol monobutyl ether; or the like may be used.

The amount of use of the 1,4-cyclohexadiene derivative represented by the formula (3) is 1 to 20 equivalents, preferably 2 to 10 equivalents, and more preferably 3 to 6 equivalents, based on the ruthenium atoms.

The method for producing the complex of the present invention may be carried out in the presence of a base. Examples of the base used herein include inorganic bases such as sodium hydroxide, sodium hydrogen carbonate, sodium carbonate, potassium hydroxide, potassium hydrogen carbonate, potassium carbonate, lithium hydroxide, lithium hydrogen carbonate, lithium carbonate, cesium carbonate, magnesium hydroxide, magnesium carbonate, calcium hydroxide, and calcium carbonate; and amines such as triethylamine, tripropylamine, tributylamine, pyridine, and triisopropylamine.

The amount of use of the base is 0.2 to 2.0 equivalents, and preferably 1.0 to 1.5 equivalents, based on the ruthenium atoms.

The reaction temperature is preferably, for example, 60° C. to 200° C., and more preferably 80° C. to 180° C.

The reaction time may vary depending on the reaction substrate used, but the reaction time is 30 minutes to 20 hours, and preferably 1 hour to 12 hours. The present method for production is preferably carried out in an inert gas such as nitrogen gas or argon gas. After completion of the reaction, the intended complex may be obtained by subjecting the reaction mixture to desired separation operations such as filtration and drying, and thus the method is very convenient in terms of operation.

In regard to the 1,4-cyclohexadiene derivative represented by the formula (3) may be produced according to a method described in, for example, Tetrahedron Letters 41 (2000) p. 6757; Synthesis (2000) p. 609; or the like, by subjecting 1,3-diene such as isoprene and an acetylene derivative having a trisubstituted silyl group, such as trimethylsilylacetylene, to the Diels-Alder reaction in the presence of a metal catalyst such as cobalt catalyst.

EXAMPLES

Hereinafter, the present invention will be described in detail by way of Examples, but the present invention is not intended to be limited to these.

Here, the $^1$H-NMR spectra for the identification of the complex and the purity determination in the following Examples and Comparative Examples were measured using a Mercury Plus 300 4N type apparatus (300 MHz) manufactured by Varian Technology Japan, Ltd.

Reference Example 1

Production of trimethyl(4-methyl-1,4-cyclohexadienyl)silane

In a four-necked flask, 1.12 g (5.1 mmol) of CoBr$_2$, 5.43 g (17 mmol) of ZnI$_2$, and 2.24 g (5.6 mmol) of diphenylphosphinoethane were dissolved in 250 ml of dichloromethane, and the solution was stirred for 30 minutes at 30° C. Subsequently, 50 ml (500 mmol) of isoprene, 63.5 ml (450 mmol) of trimethylsilylacetylene, and 1.45 g (5.6 mmol) of Bu$_4$NBH$_4$ were added thereto, and the mixture was allowed to react for one hour at 30° C. After completion of the reaction, dichloromethane was evaporated, and then the residue was distilled under reduced pressure. Thus, 68.6 g of the title compound, trimethyl (4-methyl-1,4-cyclohexadienyl) silane, was obtained at a yield of 91.7% (GC purity 80%).

$^1$H-NMR (CDCl$_3$) δ:
0.08 (s, 9H), 1.67 (s, 3H), 2.61 (m, 2H),
2.71 (m, 2H), 5.47 (m, 1H), 6.03 (m, 1H),

Example 1

Preparation of [RuCl$_2$(4-(trimethylsilyl)toluene)]$_2$

In a 50-ml Schlenk flask, 2.13 g (9.0 mmol) of ruthenium chloride trihydrate, 6.8 g (40.8 mmol) of trimethyl(4-methyl-1,4-cyclohexadienyl)silane, 0.76 g (9.0 mmol) of NaHCO$_3$, 2.3 ml of water and 22 ml of 2-methoxyethanol were added, and the mixture was allowed to react for one hour at 130° C. Subsequently, the mixture was left to cool to room temperature, and precipitated crystals were filtered. Thus, 2.06 g of the objective [RuCl$_2$ (4-(trimethylsilyl) toluene)]$_2$ was obtained at a yield of 76%.

$^1$H-NMR (CDCl$_3$) δ:
0.39 (s, 9H), 2.11 (s, 3H), 5.33 (d, 2H), 5.59 (d, 2H)

Reference Example 2

Preparation of triisopropyl(4-methyl-1,4-cyclohexadienyl)silane

In a four-necked flask, 0.27 g (1.2 mmol) of CoBr$_2$, 1.33 g (4.2 mmol) of ZnI$_2$, 0.55 g (1.4 mmol) of diphenylphosphinoethane, and 60 ml of dichloromethane were added, and the mixture was stirred for 30 minutes at 30° C. Subsequently, 12.2 ml (122 mmol) of isoprene, 20 g (110 mmol) of triisopropylsilylacetylene, and 0.35 g (1.4 mmol) of Bu$_4$NBH$_4$ were added thereto, and the mixture was allowed to react for one hour at 30° C. Dichloromethane was evaporated, and then the residue was purified by silica gel flash column chromatography. Thus, 24.6 g of the title compound, triisopropyl(4-methyl-1,4-cyclohexadienyl)silane, was obtained at a yield of 89.7% (GC purity 80%).

$^1$H-NMR (CDCl$_3$) δ:
1.05 (d, 18H), 1.17 (m, 3H), 1.66 (s, 3H), 2.65 (m, 2H), 2.71 (m, 2H), 5.42 (m, 1H), 6.02 (m, 1H)

Example 2

Preparation of [RuCl$_2$(4-(triisopropylsilyl)toluene)]$_2$

In a 150-ml Schlenk flask, 1.18 g (4.5 mmol) of ruthenium chloride trihydrate, 5.6 g (22.5 mmol) of triisopropyl(4-methyl-1,4-cyclohexadienyl)silane, 0.38 g (4.5 mmol) of NaHCO$_3$, and 11 ml of 2-methoxyethanol were added, and the mixture was allowed to react for 9 hours at 130° C. Subsequently, the mixture was left to cool to room temperature, and precipitated crystals were filtered. Thus, 1.4 g of objective [RuCl$_2$ (4-(triisopropylsilyl)toluene)]$_2$ was obtained at a yield of 73.0%.

$^1$H-NMR (CDCl$_3$) δ:
1.15 (d, 18H), 1.42 (m, 3H), 2.09 (s, 3H), 5.34 (d, 21H), 5.64 (d, 2H)

For the [RuCl$_2$(arene)]$_2$ complexes having silicon substituents obtained by the method of the present invention, and conventionally available [RuCl$_2$(arene)]$_2$ complexes having alkylbenzene for the arene moiety, the solubility in 100 ml of solvent (g/100 ml) at 25° C. in various solvents are presented in the following Table 1.

TABLE 1

| Arene | Solvent | | | | |
|---|---|---|---|---|---|
| | Methanol | THF | Toluene | Chloroform | Acetone |
| p-cymene | 3.3 | 0.7 | 0.4 | 27.9 | 0.3 |
| Benzene | 0.4 | 0.5 | 0.02 | 0.9 | 0.3 |
| Toluene | 0.16 | 0.2 | 0.02 | 0.9 | 0.14 |
| Mesitylene | 0.03 | 0.5 | 0.2 | 0.3 | 0.01 |
| TMS-tol | 3.7 | 2.3 | 1.4 | 31.3 | 1.0 |
| TIPS-tol | 2.4 | 1.9 | 1.5 | 56.5 | 0.8 |

TMS-tol: 4-Trimethylsilyltoluene
TIPS-tol: 4-Triisopropylsilyltoluene

As shown in Table 1, the complexes of the present invention have high solubility in all of polar solvents and non-polar solvents. Therefore, the ruthenium complex having a trisubstituted silyl group of the present invention may be used as catalysts at higher concentrations, as compared with the conventional ruthenium catalysts.

Example 3

Preparation of [RuCl$_2$(4-(trimethylsilyl)toluene)]$_2$

In a 50-ml Schlenk flask, 0.533 g (2.24 mmol) of ruthenium chloride trihydrate, 1.70 g (10.2 mmol) of trimethyl(4-methyl-1,4-cyclohexadienyl)silane, 0.188 g (2.24 mmol) of NaHCO$_2$, 1.17 ml of water and 10.7 ml of ethanol were added, and the mixture was allowed to react for 8 hours at a bath temperature of 90° C. The solvent was distilled off, 30 ml of pentane was added thereto, and 1.25 g of precipitated crystals was obtained. From the $^1$H-NMR measurement, the purity of [RuCl$_2$(4-(trimethylsilyl)toluene)]$_2$ was 90%.

Example 4

Preparation of [RuCl$_2$(4-(trimethylsilyl)toluene)]$_2$

In a four-necked flask, 3.00 g (11.5 mmol) of ruthenium chloride trihydrate, 9.53 g (57.4 mmol) of trimethyl(4-methyl-1,4-cyclohexadienyl)silane, 6.60 ml of water, and 60 ml of ethanol were added, and the mixture was allowed to react for 8 hours at a bath temperature of 90° C. The solvent was distilled off, 50 ml of pentane was added, and 3.63 g of precipitated crystals was obtained. From the $^1$H-NMR measurement, the purity of [RuCl$_2$(4-(trimethylsilyl)toluene)]$_2$ was 70%.

Reference Example 3

Synthesis of (4,5-dimethyl-1,4-cyclohexadienyl)trimethylsilane

In a four-necked flask, 0.54 g (2.5 mmol) of CoBr$_2$, 2.62 g (8.2 mmol) of ZnI$_2$ and 1.09 g (2.7 mmol) of diphenylphosphinoethane were dissolved in 120 ml of dichloromethane and the mixture was stirred for 0.5 hour at 30° C. Subsequently, 27.5 ml (244 mmol) of 2,3-dimethyl-1,3-butadiene, 21.5 g (219 mol) of trimethylsilylacetylene and 0.69 g (2.7 mmol) of Bu$_4$NBH$_4$ were added thereto, and the mixture was allowed to react for one hour at 30° C. After dichloromethane was evaporated under reduced pressure, 23.3 g of the title compound was obtained at a yield of 59.0% (GC purity 89%).

$^1$H-NMR (CDCl$_3$, 300 MHz) δ:
0.07 (s, 9H), 1.64 (s, 3H), 1.66 (s, 3H),
2.62 (m, 4H), 6.00 (m, 1H)

Example 5

Synthesis of [RuCl$_2$((3,4-dimethylphenyl)trimethylsilane)]$_2$

In a 50-ml Schlenk flask, 0.53 g (2.2 mmol) of ruthenium chloride trihydrate, 1.8 g (10.2 mmol) of (4,5-dimethyl-1,4-cyclohexadienyl)trimethylsilane and 0.19 g (2.2 mmol) of NaHCO$_3$ were dissolved in 11 ml of 2-methoxyethanol and 1.2 ml of water. The mixture was allowed to react for one hour at 130° C. Subsequently, the mixture was left to cool to −30° C., and precipitated crystals were filtered. Thus, 0.43 g of objective ruthenium complex was obtained at a yield of 54.8%.

$^1$H-NMR (CDCl$_3$, 300 MHz) δ:
0.39 (s, 9H), 2.03 (s, 3H), 2.14 (s, 3H), 5.30 (m, 1H), 5.38 (m, 1H), 5.48 (m, 1H).

The invention claimed is:

1. A ruthenium complex represented by the following formula (1):

wherein X represents a halogen atom; L$^1$ represents an aromatic compound represented by the following formula (2):

(wherein R$^1$, R$^2$, R$^3$, R$^4$, R$^5$ and R$^6$ each independently represent an alkyl group having 1 to 10 carbon atoms, a cycloalkyl group having 3 to 6 carbon atoms, or a phenyl group which may be substituted with an alkyl group having 1 to 10 carbon atoms or an alkoxy group having 1 to 10 carbon atoms; R$^7$ and R$^8$ each independently represent a hydrogen atom, an alkyl group having 1 to 10 carbon atoms, or an alkoxy group having 1 to 10 carbon atoms; and n1, n2 and n3 each represent 0 or 1).

2. A method for producing the ruthenium complex according to claim 1, the method comprising reacting ruthenium halide or a hydrate thereof with a diene compound represented by the following formula (3) in a solvent:

wherein R$^1$, R$^2$, R$^3$, R$^4$, R$^5$ and R$^6$ each independently represent an alkyl group having 1 to 10 carbon atoms, a cycloalkyl group having 3 to 6 carbon atoms, or a phenyl group which may be substituted with an alkyl group having 1 to 10 carbon atoms or an alkoxy group having 1 to 10 carbon atoms; and R$^7$ and R$^8$ each independently represent a hydrogen atom, an alkyl group having 1 to 10 carbon atoms, or an alkoxy group having 1 to 10 carbon atoms; and n1, n2 and n3 each represent 0 or 1.

3. The method for producing the ruthenium complex according to claim 2, wherein the reaction is carried out in the presence of a base.

4. The method for producing the ruthenium complex according to claim 2, wherein the ruthenium halide is ruthenium chloride.

5. The method for producing the ruthenium complex according to claim 3, wherein the ruthenium halide is ruthenium chloride.

* * * * *